US005624433A

United States Patent [19]

Radisch, Jr.

[11] Patent Number: 5,624,433
[45] Date of Patent: Apr. 29, 1997

[54] ANGIOPLASTY BALLOON WITH LIGHT INCISOR

[75] Inventor: Herbert R. Radisch, Jr., San Diego, Calif.

[73] Assignee: Interventional Technologies Inc., San Diego, Calif.

[21] Appl. No.: 429,917

[22] Filed: Apr. 24, 1995

[51] Int. Cl.$^6$ .................................................. A61B 17/36
[52] U.S. Cl. ........................................ 606/7; 606/15
[58] Field of Search ............................. 606/4, 5, 6, 7, 606/10, 11, 12, 14, 15, 16, 17

[56] References Cited

U.S. PATENT DOCUMENTS

| | | |
|---|---|---|
| 3,635,223 | 1/1972 | Klieman . |
| 4,140,126 | 2/1979 | Choudhury . |
| 4,263,236 | 4/1981 | Briggs et al. . |
| 4,273,128 | 6/1981 | Lary . |
| 4,292,974 | 10/1981 | Fogarty et al. . |
| 4,608,984 | 9/1986 | Fogarty . |
| 4,627,436 | 12/1986 | Leckrone . |
| 4,685,458 | 8/1987 | Leckrone . |
| 4,723,549 | 2/1988 | Wholey et al. . |
| 4,886,061 | 12/1989 | Fischell et al. . |
| 4,966,604 | 10/1990 | Reiss . |
| 5,009,659 | 4/1991 | Hamlin et al. . |
| 5,196,024 | 3/1993 | Barath . |
| 5,209,799 | 5/1993 | Vigil . |
| 5,226,430 | 7/1993 | Spears et al. ........................ 606/7 |
| 5,226,887 | 7/1993 | Farr et al. . |
| 5,248,311 | 9/1993 | Black et al. ....................... 606/17 |
| 5,320,634 | 6/1994 | Vigil . |
| 5,395,361 | 3/1995 | Fox et al. ........................... 606/16 |
| 5,411,466 | 5/1995 | Hess ................................. 606/7 X |
| 5,415,654 | 5/1995 | Daikuzono ........................ 606/15 |
| 5,417,653 | 5/1995 | Sahota et al. ..................... 606/7 X |
| 5,437,659 | 8/1995 | Leckrone ........................... 606/7 |
| 5,456,681 | 10/1995 | Hajjar ............................... 606/16 |
| 5,496,308 | 3/1996 | Brown et al. .................... 606/17 |

FOREIGN PATENT DOCUMENTS 3400416 7/1985 Germany .
3402573 8/1985 Germany .
WO90/07909 7/1990 WIPO .

OTHER PUBLICATIONS

B.G. Lary, M.D., *Experimental Maintenance of Life by Intravenous Oxygen, Preliminary Report*, Clinical Congress of the American College of Surgeons, San Francisco, Nov. 5–9, 1951.

Banning G. Lary, M.D., *Effect of Endocardial Incisions on Myocardial Blood Flow*, Archives of Surgery, Sep. 1963, vol. 87, pp. 424–427 (reprint).

Banning G. Lary, M.D., *Method for Increasing the Diameter of Long Segments of the Coronary Artery*, The American Surgeon, Jan., 1966, vol. 32, No. 1, pp. 33–35 (reprint).

Banning G. Lary, M.D., John G. Chesney, M.D., Thomas O. Gentsch, M.D., F.C.C.P. and Parry B. Larsen, M.D., *The "Coronary Myocardial Artery" for Coronary Artery Disease*, Diseases of the Chest, vol. 49, No. 4, Apr., 1966, pp. 412–419 (reprint).

Banning G. Lary, M.D., *Onlay Vein Graft for the Correction of Coronary Artery Obstruction*, Surgery, vol. 59, No. 4, pp. 547–551, Apr., 1966 (reprint).

Banning G. Lary, M.D. and Roger W. Sherman, M.D., *A Method for Creating a Coronary–Myocardial Artery*, Surgery, vol. 59, No. 6, pp. 1061–1064, Jun., 1966.

(List continued on next page.)

*Primary Examiner*—Angela D. Sykes
*Assistant Examiner*—Sonya Harris-Ogugua
*Attorney, Agent, or Firm*—Nydegger & Associates

[57] ABSTRACT

A device for incising and dilating a stenosis in a vessel of a patient includes a catheter having an inflatable balloon near its distal end. A laser rod formed with a light groove on its distal portion is bonded to the catheter with the light groove positioned on the balloon. In the operation of the device, the catheter and laser rod are inserted through the vessel to place the balloon and light groove in contact with the stenosis. Laser light is then directed through the laser rod for emission from the light groove to incise the stenosis. Simultaneously, the balloon is inflated. This inflation of the balloon causes further incision of the stenosis and dilatation of the stenosis.

12 Claims, 2 Drawing Sheets

OTHER PUBLICATIONS

Banning G. Lary, *A Method to Create and Correct Stenosis of a Coronary Artery*, Archives of Surgery, vol. 93, pp. 828–830, Nov. 1966.

Banning G. Lary, *An Epicardial Purse String Suture for Closing Coronary Arteriotomy*, The American Surgeon, No. 3, pp. 213–214, Mar. 1967.

Banning G. Lary, M.D., *Surgery for Coronary Artery Disease*, Nursing Clinics of North America, vol. 2, No. 3, pp. 537–542, Sep., 1967.

Banning G. Lary, M.D., Antonio Camelo, M.D., Roger W. Sherman, M.D., and Thomas J. Noto, N.D., *Myocardial Revascularization Experiments Using the Epicardium*, Archives of Surgery, vol. 98, pp. 69–72, Jan., 1969.

Banning G. Lary, M.D., *Coronary Artery Resection and Replacement by a Blood Conduit*, Surgery, vol. 65, No. 4, pp. 584–589, Apr., 1969.

Banning G. Lary, M.D., Roger W. Sherman, M.D., Sonya S. Glasser, Joan McDermott, and Frank Gollan, M.D., *Experimental Vein Angioplasty of the Circumflex Coronary Artery*, Journal of Surgical Research, vol. 17, pp. 210–214, 1974.

Banning G. Lary, M.D., *Coronary Artery Incision and Dilation*, Archives of Surgery, vol. 115, pp. 1478–1480, Dec., 1980.

5,624,433

ANGIOPLASTY BALLOON WITH LIGHT INCISOR

FIELD OF INVENTION

The present invention pertains generally to surgical devices which are useful for clearing a stenosis from the vessel of a patient. More particularly, the present invention pertains to angioplasty devices which both incise and dilate the stenosis. The present invention is particularly, but not exclusively, useful for dilating the stenosis with an inflatable balloon and incising the stenosis with laser light energy from a laser rod which is mounted on the balloon.

BACKGROUND OF THE INVENTION

Many medical complications are created by the total or even partial blockage of blood vessels of the body. The primary cause of these complications is, of course, the reduction or cessation of blood flow through the blocked vessels to the particular biological tissue which is fed by the vessel. Most commonly, a blockage, or stenosis, is formed in an artery as a result of plaque build-up in the artery. Further, it is not uncommon for several stenoses to occur sequentially in a single artery or to develop near one another in branches of a common central artery.

Several methods, or procedures, have been developed in the medical field for the purpose of removing or clearing stenoses from the vessels of patients. One well known procedure for accomplishing this is an angioplasty procedure such as is disclosed in U.S. Pat. No. Re. 33,561 which issued to Levy for an invention entitled "BALLOON AND MANUFACTURE THEREOF". Basically, in an angioplasty procedure, a deflated dilatation balloon is inserted into the vessel and is placed across the stenosis. Once the balloon is properly positioned, it is then inflated to dilate the artery and thereby clear the stenosis. Another, more recently developed procedure for clearing a stenosis, is an atherectomy procedure. The essential aspects of an atherectomy procedure are set forth in U.S. Pat. No. 4,895,166 which issued to Farr et al. for an invention entitled "ROTATABLE CUTTER FOR THE LUMEN OF A BLOOD VESSEL". As disclosed by Farr et al., in an atherectomy procedure the stenotic material is actually cut and removed from the artery.

Both the angioplasty procedure and the atherectomy procedure are typically accomplished indirectly wherein access to the stenosis is achieved through a peripheral artery. These procedures are in contrast to other known procedures used to clear arteries, such as a by-pass surgery, where direct access to the stenosis is achieved by entering the artery at or near the site of the stenosis. Despite their differences, the ultimate objective of all these procedures is to remove or alleviate the stenosis which is restricting blood flow through the artery.

Recent studies have indicated that for procedures wherein a stenosis is to be dilated, such as for an angioplasty procedure, the efficacy of the dilatation is enhanced by first incising the material which is creating the stenosis. With this knowledge, several devices for clearing blocked arteries have been proposed.

For example, U.S. Pat. No. 5,209,799 which issued to Vigil for an invention entitled "METHOD FOR MANUFACTURING A FOLDING BALLOON CATHETER" discloses a folding angioplasty balloon with attached atherotomes. Operationally, the atherotomes attached to the Vigil device are intended to produce a series of incisions in the stenosis as the angioplasty device is inflated, thereby reducing the force needed to dilate the stenosis.

In general, the use of attached atherotomes has been found to be highly efficacious. As a result, the basic idea of attaching atherotomes to an angioplasty balloon has led to the development of folding devices, like the Vigil device, which conceal the atherotomes until the balloon is inflated. It may be appreciated that concealment of the atherotomes, as accomplished by Vigil, fathers an important goal by preventing unwanted contact between the atherotomes and the patient's vascular system as the balloon is maneuvered into position across the stenosis.

One way in which the functionality of traditional angioplasty balloons may be improved, that may not be entirely addressed through the use of attached atherotomes, is the provision of an angioplasty balloon with may be controlled to produced incisions of varying depth. In greater detail, it may be appreciated that a particular stenosis may require either a large or a small amount of incision before an effective dilation may be performed. If an atherotome equipped balloon is used, however, the degree to which the stenosis will be incised will be determined by the size of the atherotomes attached to the balloon, effectively limiting the degree to which the incision depth may be varied.

In light of the above, it is an object of the present invention to provide a device and method for incising and dilating a stenosis in a vessel of a patient which provides the ability to control the depth of incisions created. Another object of the present invention is to provide a device and method for incising and dilating a stenosis in a vessel of a patient which protects the vessel from unwanted incisions as the device is positioned within the stenosis. Yet another object of the present invention is to provide a device and method for incising and dilating a stenosis in a vessel of a patient which is relatively simple to manufacture, is easy to use, and is comparatively cost effective.

SUMMARY OF THE INVENTION

In accordance with the present invention, a device and method for dilating and incising a stenosis in a vessel of a patient includes a catheter which is formed with a guidewire lumen and an inflation lumen. An inflatable balloon is mounted near the distal end of the catheter and the balloon may be selectively inflated by introducing fluid into the balloon through the inflation lumen. More specifically, the inflatable balloon is formed with a distal dilatation section and a proximal tapered section. The dilatation section is essentially tubular shaped with a substantially constant diameter, and the tapered section is substantially cone shaped with a proximally decreasing cross section.

A laser rod having a distal portion and a proximal portion is formed with a light groove along its distal portion. The light groove is substantially V-shaped and is formed to capture and emit laser light from the rod in a predictable manner. The laser rod itself is mounted directly onto the catheter. The laser rod itself is also mounted directly onto the inflatable balloon, with the distal portion of the rod bonded to the dilatation section of the balloon, and with the proximal portion of the laser rod spiraled around the catheter.

In the operation of the device of the present invention, a guidewire is first inserted through the vessel of the patient to the stenosis. The guidewire is then inserted into the guidewire lumen of the catheter and the catheter is advanced over the guidewire to position the balloon and the distal portion of the laser rod against the stenosis. Light from a laser source is then directed through the laser rod for emission from the light groove to incise the stenosis. While the laser light from the laser rod is incising the stenosis, the inflatable balloon is inflated. This inflation urges the light groove and the balloon against the stenosis to simultaneously incise and dilate the stenosis.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
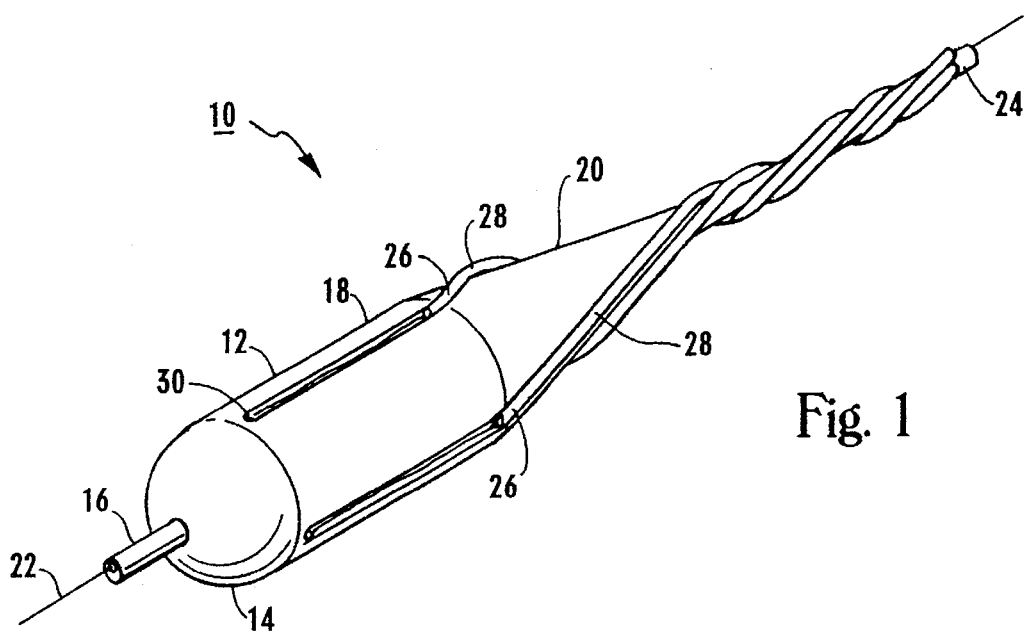
FIG. 1 is an isometric view of the present invention.

The present invention provides a device and method for incising and dilating a stenosis in a blood vessel of a patient. Referring initially to FIG. 1, it may be seen that the device 10 includes an inflatable balloon 12. In greater detail, it may be seen that the balloon 12 includes a rounded distal end 14 formed around a lumen 16. The distal end 14 is joined to a dilation section 18 which is substantially cylindrical or tubular in shape. In turn, the dilation section 18 joins a conically shaped tapered section 20. For the purposes of illustration, it should be noted that the distal end 14, dilation section 18 and tapered section 20 define a central or longitudinal axis 22. A tubular catheter 24 is attached to the tapered section 20. Preferably, the distal end 14, dilation section 18 and tapered section 20 are formed as a single piece of high-density polymeric material.

A series of laser rods 26 are mounted on the dilation section 18 of the balloon 12. Each of the laser rods is mounted to substantially parallel the longitudinal axis 22 and each is connected to a light conduit 28 at the point where the dilation section 18 merges into the tapered section 20. Each light conduit 28 is spirally wound around the tapered section 20 and the spiral winding continues as the tapered section 20 merges into the tubular catheter 24. The spiral winding continues so that each of the light conduits 28 spans the length of the tubular catheter 24. Preferably, the light conduits 28 are fabricated as fiber-optic elements.

Figure 2:
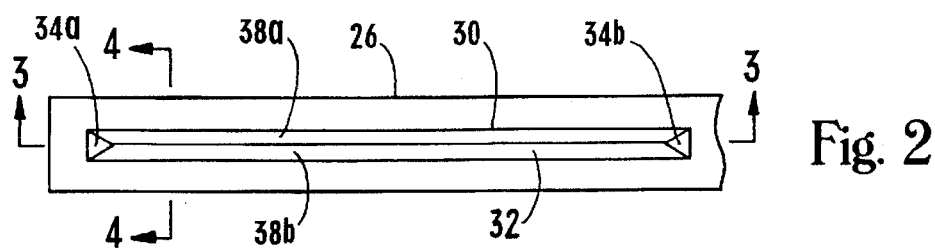
FIG. 2 is a top elevational view of the distal end of a laser rod of the present invention showing the light groove of the present invention.
Figure 3:
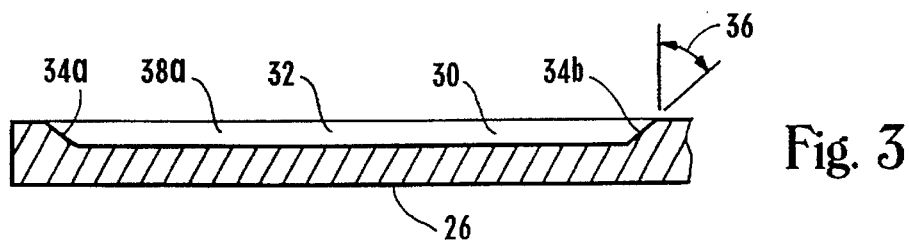
FIG. 3 is a sectional view of the laser rod of the present invention taken along the line 3—3 of FIG. 2 showing the light groove of the present invention.
Figure 4:
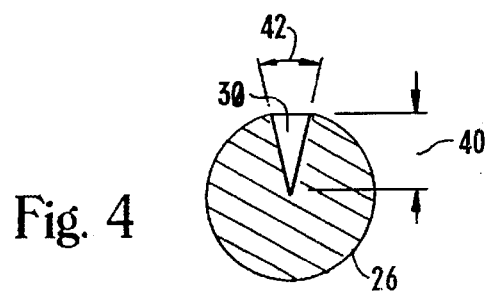
FIG. 4 is a sectional view of the laser rod of the present invention taken along the line 4—4 of FIG. 2 showing the light groove of the present invention.

The structural details of the laser rods 26 may be better seen by reference to FIGS. 2 through 4. Referring initially to FIG. 2 it may be seen that each of the laser rods 26 includes a light groove 30 formed as a narrow trough 32. Importantly, and as shown in FIGS. 3 and 4, the trough 32 of the light groove 30 is bounded by two sloping end surfaces 34a and 34b. For purposes of illustration, the angle of inclination of the end surfaces is shown and designated 36. Preferably, the angle 36 measures forty-five (45) degrees.

In addition to the two end surfaces 34a and 34b, the trough 32 has two sides 38a and 38b. The two sides 38a and 38b converge to give the trough 32 a V-shape best seen in FIG. 4. The V-shape trough is further defined by a depth 40 and an angle 42. It may be appreciated that the particular values chosen for angle 42, depth 40 and angle 36 are intended to produce an optical flaw allowing light to escape from trough 32. Therefore, angle 42 is preferably ten to thirty degrees (10°–30°) and depth 40 is preferably chosen to extend trough 32 to at least the center of laser rod 26.

Figure 5:
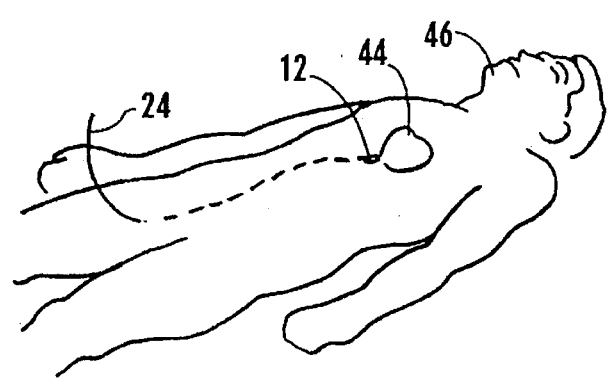
FIG. 5 is a perspective view of the present invention operationally positioned in a blood vessel near the heart of a patient.

The intended environment for the present invention may be seen in FIG. 5 where the balloon 12 of the present invention is shown positioned near the heart 44 of a patient 46. FIG. 5 also shows the tubular catheter 24 extending into the patient 46 and connected to the balloon 12. The use of the present invention may be seen in greater detail in FIG. 6 where it may be seen that the balloon 12 has been positioned over a guidewire 48. The guidewire has a distal end 50 and a proximal end 52 and the combination of the guidewire 48 and balloon 12 have been positioned within the stenosis 54 which has partially occluded a vessel 56. Additionally, the tubular catheter 24 and series of light conduits 28 have been connected to a control unit 58 which includes a hydraulic pressure supply 60 and a laser light source 62. It may be appreciated that the vessel 56, shown in FIG. 6 is intended to be exemplary and typical of vessels that might be found in patient 46 especially near the heart 44.

OPERATION

Figure 6:
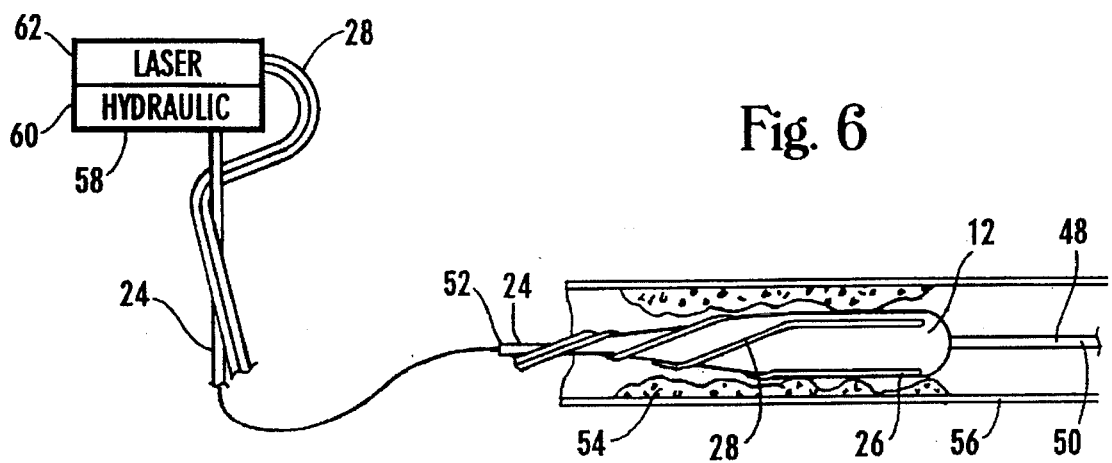
FIG. 6 is a side elevational view of the balloon of present invention operationally positioned across a stenosis in a blood vessel, with the balloon shown connected to a control unit and the blood vessel shown in cross section.

Use of the present invention is, perhaps, best appreciated by reference to FIG. 6 and begins by insertion of the distal end 50 of the guidewire 48 into the vessel 56. The distal end 50 is advanced in the vessel 56 until it has passed the stenosis 54 which is the target of the procedure. After the guidewire 48 has been inserted, the proximal end 52 of the guidewire 48 is inserted through the lumen 16 and balloon 12 and into the catheter 24. The balloon 12 is then advanced over the guidewire 48 and through the vessel 56 until the balloon 12 is positioned within the stenosis 54.

Once the balloon 12 is positioned within the stenosis 54, the laser light source 62 in the control unit 58 is used to energize the series of laser conduits 28. The laser energy travels through the laser conduits 28 into the laser rods 26 energizing the laser rods 26. The light groove 30 included in each laser rod 26 focuses and projects the laser energy supplied to the laser rod 26 by the laser light source 62. Specifically, the geometry chosen for the light groove 30 causes the laser energy to be focused along a line which substantially spans the length of the light groove 30 and which is projected radially away from the balloon 12 and longitudinal axis 22.

The energy emitted by the light grooves 30 cuts into tissue of the stenosis 54 by photoablation to create a series of incisions in the stenosis 54. As the stenosis 54 is incised, fluid supplied by the hydraulic pressure supply 60 of the control unit 58 is passed through the tubular catheter 24 to inflate the balloon 12. The inflation of the balloon 12 applies a dilating force to the stenosis 54 expanding the stenosis 54 and partially or fully restoring circulation through the vessel 56. After dilation, laser light source 62 is deactivated and the fluid supplied by the hydraulic pressure supply 60 of the control unit 58 is withdrawn to deflate balloon 12.

The processes of incising and dilating the stenosis 54 may be repeated one or more times, as required to remove the occluding stenosis 54. After the stenosis 54 is cleared, the balloon 12 and guidewire 48 are withdrawn, completing the procedure.

While the particular device and method for incising and dilating a stenosis as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A device for dilating a stenosis in a vessel which comprises:

a laser rod having a distal portion, said distal portion of said laser rod being formed with a light groove for emitting laser light from said rod to incise the stenosis;

means for placing said distal portion of said laser rod against the stenosis;

means for directing laser light through said laser rod for emission from said light groove;

an inflatable balloon mounted on said placing means and having an exterior surface for urging said distal portion of said laser rod against the stenosis, wherein said distal portion of said laser rod is bonded to said exterior surface of said balloon.

2. A device as recited in claim 1 wherein said placing means is a catheter, said catheter defining an axis.

3. A device as recited in claim 2 wherein said laser rod has a proximal portion and said proximal portion of said laser rod is spiraled around said catheter.

4. A device as recited in claim 2 wherein said inflatable balloon is mounted on said catheter.

5. A device as recited in claim 4 wherein said inflatable balloon includes a dilatation section and a tapered section, said tapered section being proximal to said dilatation section and tapered with diminishing cross section in the proximal direction.

6. A device as recited in claim 5 wherein said light groove is substantially aligned parallel to said axis.

7. A device as recited in claim 2 wherein said light groove is formed with opposing side surfaces to create a V-shape for said light groove, said side surfaces expending generally parallel to said axis.

8. A device as recited in claim 7 wherein said light groove is further formed with a distal end surface and a proximal end surface, said distal end surface and said proximal end surface forming an approximately forty-five degree angle with said axis.

9. A device as recited in claim 2 wherein said catheter is formed with a lumen and said device further comprises a guidewire insertable through said lumen for guiding said catheter to the stenosis.

10. A device as recited in claim 2 wherein said laser light directing means further comprises a source of laser light.

11. A dilatation balloon as recited in claim 1 wherein said catheter is formed with a lumen and said dilating balloon further comprises a guidewire prepositionable in the vessel of the patient and insertable into said lumen of said catheter for advancing said dilatation balloon with said laser light rod to a stenosis in the vessel to incise and dilate the stenosis.

12. A dilatation balloon with laser light incisor for incising and dilating a stenosis in a vessel of a patient which comprises:

a catheter formed with a lumen;

an expandable dilatation balloon surroundingly attached to said catheter, said balloon being tapered with a proximally decreasing cross section;

at least one laser light rod, said laser light rod having a distal section mounted on said balloon, and said section being formed with an elongated longitudinal groove for concentrating and emitting laser light therefrom;

means in fluid communication with said balloon for selectively inflating said balloon; and a laser light source connected in light communication with said laser light rod for flooding said laser light rod with laser light.

* * * * *